United States Patent [19]

Luo et al.

[11] Patent Number: 4,534,786
[45] Date of Patent: Aug. 13, 1985

[54] 1-ALKYL DERIVATIVES OF 3-ARYLOXY-4-(2-CARBALKOXY)-PHENYL-AZET-2-ONES AS PLANT GROWTH REGULATORS

[75] Inventors: Tatao Luo, El Sobrante; Louis Russo, Walnut Creek; Francis J. Freenor, III, Richmond, all of Calif.

[73] Assignee: Chevron Research Company, San Francisco, Calif.

[21] Appl. No.: 600,260

[22] Filed: Apr. 13, 1984

Related U.S. Application Data

[62] Division of Ser. No. 391,798, Jun. 23, 1982, Pat. No. 4,443,372.

[51] Int. Cl.$^3$ .............................................. A01N 43/44
[52] U.S. Cl. ............................................. 71/88; 71/76
[58] Field of Search ........................................ 71/89, 76

[56] References Cited

U.S. PATENT DOCUMENTS

| | | | |
|---|---|---|---|
| 3,958,974 | 5/1976 | Hotz et al. ............................... | 71/88 |
| 4,075,000 | 2/1978 | Abdulla .................................... | 71/88 |
| 4,181,800 | 1/1980 | Kamiya et al. ......................... | 544/180 |
| 4,207,234 | 6/1980 | Kamiya et al. ......................... | 260/239 A |
| 4,294,606 | 10/1981 | Tobler et al. ........................... | 71/88 |

Primary Examiner—Catherine L. Mills
Attorney, Agent, or Firm—S. R. LaPaglia; T. G. DeJonghe; S. L. Biggs

[57] ABSTRACT

1-Alkyl derivatives of 3-aryloxy-4-(2-carbalkoxy)-phenyl-azet-2-ones of the formula:

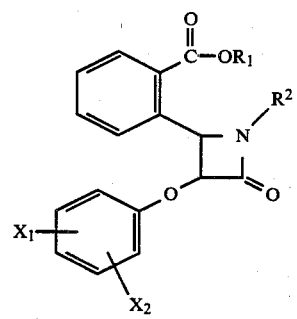

wherein $R_1$ is methyl or ethyl; $R_2$ is lower alkyl; and $X_1$ and $X_2$ are independently hydrogen or halogen, are effective as plant growth regulators.

24 Claims, No Drawings

1-ALKYL DERIVATIVES OF 3-ARYLOXY-4-(2-CARBALKOXY)-PHENYL-AZET-2-ONES AS PLANT GROWTH REGULATORS

This is a division of application Ser. No. 391,798 filed June 23, 1982, now U.S. Pat. No. 4,443,372.

BACKGROUND OF THE INVENTION

The present invention relates to novel 1-lower alkyl derivatives of 3-aryloxy-4-(2-carbalkoxy)-phenylazet-2-ones which are active as plant growth regulators.

The commonly assigned patent application Ser. No. 225,886 of Francis J. Freenor III, now U.S. Pat. No. 4,456,467, discloses compounds of the formula:

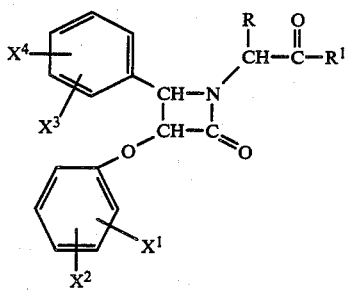

wherein R is hydrogen or alkyl of 1 to 3 carbon atoms; $R^1$ is hydrogen, alkyl of 1 to 6 carbon atoms, alkoxy of 1 to 6 carbon atoms, alkylthio of 1 to 6 carbon atoms or $NR^1R^2$ wherein $R^1$ and $R^2$ are independently hydrogen or alkyl of 1 to 12 carbon atoms; and $X^1$, $X^2$, $X^3$ and $X^4$ are independently hydrogen, chloro, bromo, fluoro, iodo, alkyl of 1 to 4 carbon atoms or alkoxy of 1 to 4 carbon atoms, which are active as plant growth regulators.

U.S. Pat. No. 4,181,800 discloses a large group of anti-microbial 2-azetidinone compounds of the general formula:

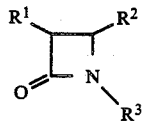

wherein $R^1$ is amino, substituted amino, substituted hydroxy, azido or halogen; $R^2$ is hydrogen, hydroxymethyl, aralkoxyaminomethyl, aryl, aralkenyl, formyl, carboxy, or a residue of a nucleophile; and $R^3$ is a group of the formula:

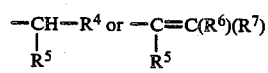

wherein $R^2$ is aryl, aralkyl, arylthioalkyl or a heterocyclic group; $R^5$ is carboxy or its derivative; $R^6$ is alkyl, haloalkyl, arylthio or heterocyclic-thioalkyl; and $R^7$ is hydrogen, haloalkyl or heterocyclic-thioalkyl; (subject to various provisos). The compounds are disclosed as useful antibiotics for treating microbial infections in mammals.

U. S. Pat. No. 4,207,234 discloses a large class of anti-microbial 4-unsubstituted azetidinone compounds which have the general formula:

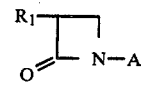

wherein $R_1$ is amino or acylamino; and A is hydrogen or the group:

wherein $R^x$ is hydrogen; $R^y$ is, in pertinent part, hydrogen or alkyl of up to 6 carbon atoms; and $R^2$ is, in pertinent part, carboxy, hydroxy, amino, cyano, or alkyl of up to 6 carbon atoms substituted by carboxy or a salt thereof. These compounds are disclosed as useful as antibiotics to treat microbial infections in mammals.

SUMMARY OF THE INVENTION

The plant growth regulating 1-lower alkyl derivatives of 3-aryloxy-4-(2-carbalkoxy)-phenyl-azet-2-one compounds of this invention are represented by the formula:

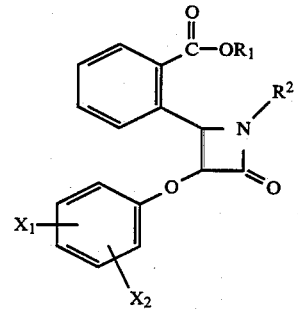

wherein $R_1$ is methyl or ethyl; $R_2$ is lower alkyl; and $X_1$ and $X_2$ are independently hydrogen or halogen.

Among other factors, the present invention is based on our finding that these compounds show surprising activity as plant growth regulators. In particular, treatment of plants with the compounds of our invention may result in increased yields in crops. The plant growth regulating activity of the compounds of this invention is very susceptible to structural change, such that while the compounds of this invention having a carbalkoxy group in the ortho position on the 4-phenyl group show unexpectedly good activity as plant growth regulators, corresponding compounds having the carbalkoxy group in the meta or para position on the 4-phenyl group show significantly less activity as plant growth regulators. It is believed that the trans isomer of these compounds, that is, where the 3-phenoxy and the 4-phenyl groups are in the trans position, has greater activity than the corresponding cis isomer.

The plant growth regulating activities of the compounds of this invention include increased side branching in plants, bud break at nodes which do not normally produce branches, and increased flower set resulting in increased yeilds. The compounds of this invention are useful in increasing the yields in crops such as pinto beans, soybeans, sunflowers, peanuts, corn and other similar crops.

As is apparent, the compounds have asymmetric carbon atoms and thus can exist as optical isomers. Accordingly, the respective optical isomers and geometric isomers, as well as mixtures thereof, are encompassed within the invention.

Representative $R_2$ groups include methyl, ethyl, n-propyl, isopropyl, isobutyl, and hexyl.

Preferred are compounds where one of $X_1$ and $X_2$ is halogen.

Especially preferred are compounds where $R_1$ is methyl, and $R_2$ is isopropyl.

As used herein, the following terms have the following meanings, unless expressly stated to the contrary.

The term "alkyl" refers to both straight- and branched-chain alkyl groups. The term "lower alkyl" refers to both straight- and branched-chain groups having a total of from 1 to 6 carbon atoms and includes primary, secondary and tertiary alkyl groups. Typical lower alkyls include, for example, methyl, ethyl, n-propyl, isopropyl, and the like.

The term "halo" or "halogen" refers to the groups fluoro, chloro, bromo, and iodo.

The term "carbalkoxy" refers to the

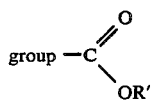

where R' is an alkyl group. The term "lower carbalkoxy" refers to carbalkoxy groups where R' is a lower alkyl group. Typical carbalkoxy groups include carbomethoxy, carbethoxy, and the like.

The terms "plant growth regulator" and "plant growth regulating" refer to compounds and/or their activities which alter growth or development of a plant as by a direct or indirect effect on natural phytohormone systems which may result in a beneficial increase or decrease in growth rate of the entire plant or a specific plant organ, or by helping a plant to adjust to stress, as by increased tolerance to drought, salt or wind. These growth regulating effects include, but are not limited to, increased branching, bud break at nodes which do not normally produce branches, increased or decreased set of flowers, reduction of stem height, preventing or retarding the growth of lateral buds, and promotion of the thinning out of superfluous fruits in various fruit trees.

DETAILED DESCRIPTION OF THE INVENTION

The compounds of the present invention may be prepared according to the following reaction sequence:

(1)

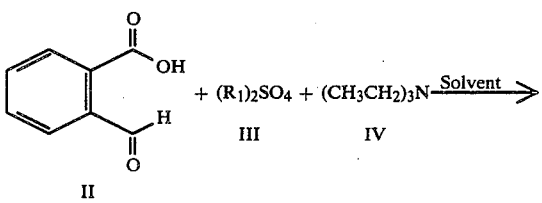

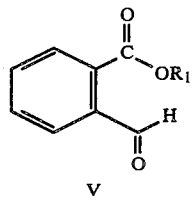

V (2)

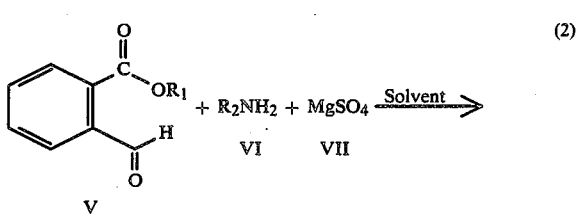

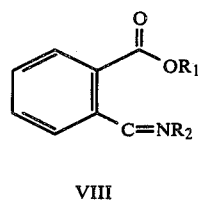

VIII (3)

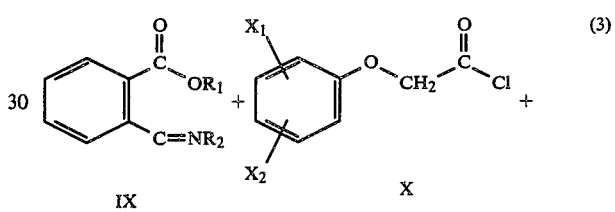

$(CH_3CH_2)_3N \xrightarrow{\text{hexane}}{\text{toluene}}$

XI

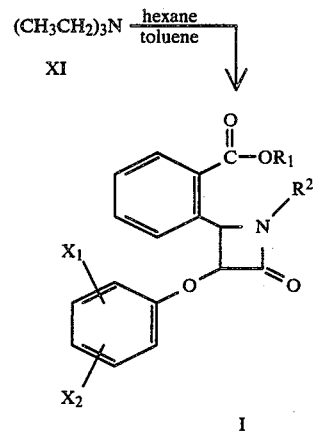

I

Reaction (1) is carried out by adding IV to a warmed, stirred mixture of II and III in solvent at a rate of addition that will maintain a brisk reflux. Suitable solvents include inert organic solvents such as methylene chloride, chloroform or toluene. The preferred molar ratios for the reactants are 2 moles of each III and IV per mole of II, although ratios somewhat less or greater may be employed. After the addition of IV is complete, the stirred mixture is allowed to come to ambient temperature.

Reaction (2) is carried out by slowly adding a mixture of VI in solvent to a stirred mixture of V and VII in solvent. The temperature is maintained in the range of about 20°–35° C. during the addition. After the addition is complete, the reaction mixture is stirred for a period of time, from about 0.5 to about 3 hours. Suitable solvents include inert organic solvents such as methylene chloride or chloroform. The molar ratio of V to VI is approximately equal, although slightly higher or lower ratios may be used. The product VIII may then be isolated by conventional procedures such as filtration, extraction, washing, or stripping under reduced pressure and heat.

Reaction (3) is carried out by the slow addition of X in toluene to a mixture of IX in hexane. The temperature is maintained around 30° C. during the addition. The XI is then added. During the addition, the temperature of the reaction mixture increases due both to warming of the solution and the exothermic addition. The mixture is allowed to stir for a period of about 1 to 8 hours. The product I may be isolated by conventional procedures such as filtration, extraction, washing, stripping under reduced pressure and heat, hard topping and chromatography.

The above reaction sequence results in a product I which is a mixture of cis and trans isomer.

Pure cis isomer and also a mixture containing predominantly trans isomer, may be separated from a mixture of cis and trans isomers by conventional separation processes such as chromatography.

The cis isomer product I may be prepared by carrying out Reaction (3) in a slightly different manner. Reactions (1) and (2) are carried out as described previously. To produce cis-I, Reaction (3) is carried out by the dropwise addition of X in toluene to a stirred mixture of IX and XI in toluene over a period of time, maintaining the temperature of the reaction mixture in the range of about 35°–40° C. The mixture is allowed to stir for about 1 hour. The cis-I may be isolated by conventional procedures such as filtration, extraction, washing, stripping under reduced pressure and heat, hard topping and chromatography.

Utility

The compounds of the present invention are surprisingly active as plant growth regulators, and effect plant growth in a variety of ways.

The plant growth regulating effects of the compounds of this invention include increasing the number of flowers set in, for example, pinto beans. This results in a greater number of pods, and thus a greater yield. These compounds also may cause increased side branching in plants, resulting in a shorter, more compact plant. These compounds also may cause bud break at nodes which do not normally produce branches. In addition, these compounds may alter tropisms, such as geotropism, in plants.

A further understanding of our invention can be had from the following nonlimiting examples.

EXAMPLE 1

Preparation of

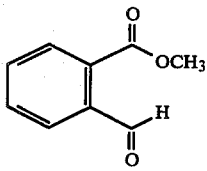

In a 1-liter, 3-necked, round-bottom flask with drying tube, condenser, thermometer, stirrer and dropping funnel, 80 grams (0.5329 moles) of

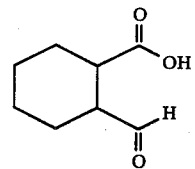

134.42 grams (1.0758 moles) dimethylsulfate, and 120 mls methylene chloride were placed and the resulting slurry stirred.

The flask was then warmed to 45° C. and the addition of 113.23 grams of triethylamine was begun. The rate of addition of triethylamine was adjusted to maintain a brisk reflux. During the course of the addition which took about 30 minutes, the temperature of the reaction mixture increased to 58° C. After the addition was complete, the reaction mixture was allowed to stir while its temperature came to 25° C.

To the reaction mixture, 200 mls of ice water were then added, decreasing the temperature to 22° C. The resulting mixture was stirred for about 10 minutes and the phases were then separated. The upper water layer was washed once with about 50 mls methylene chloride which was then combined with the organic layer. The combined organic layers were then washed once with about 100 mls water, followed by about 100 mls sodium bicarbonate solution (50 mls saturated sodium bicarbonate solution and 50 mls water), and again by about 100 mls water. The organic layer was then dried over magnesium sulfate; silica gel was added and then filtered, rinsing the solids with methylene chloride. Stripping of the methylene chloride gave 83.27 grams of the product, a light tan oil. The IR and NMR spectra were consistent with very pure compound.

EXAMPLE 2

Preparation of

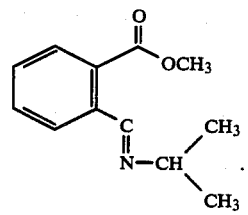

In a 500-ml, 3-necked, round-bottom flask wth nitrogen atmosphere, drying tube, condenser, thermometer, stirrer and dropping funnel, 32.83 grams of the product of Example 1, about 10 grams magnesium sulfate and 40 mls of methylene chloride were placed. To the resulting mixture, 12 grams isopropylamine in 20 mls methylene chloride were slowly added using the dropping funnel. During the addition, the temperature of the reaction mixture was kept at about 27°–29° C. The reaction mixture was then allowed to stir for about 1 hour and 15 minutes. The reaction mixture was filtered, rinsing the solids with methylene chloride. Stripping of the methylene chloride gave 40.72 grams of the product, a pale oil. The product was used immediately in Example 3.

EXAMPLE 3

Preparation of

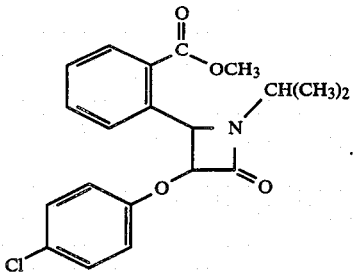

In a 500-ml, 3-necked, round-bottom flask with nitrogen atmosphere, drying tube, condenser, thermometer, stirrer and dropping funnel, 38.14 grams α-(4-chlorophenoxy)acetyl chloride and 50 mls hexane were placed. To the resulting mixture, the product of Example 2 in 15 mls dry toluene were added slowly. During the first half of the addition, the temperature was maintained at about 31°–33° C. The addition resulted in a very thick slurry, not all of which stirred, so 20 mls of toluene were added, resulting in freer stirring, and the mixture was heated to 47° C. and held there for about 15 minutes. To the slurry, 19.23 grams triethylamine were added slowly. The temperature at the beginning of the addition was 43° C.; the temperature then decreased to 40° C. at the end of the addition. The mixture was heated, after about 15 minutes reaching 49° C. then increasing exothermically to 65° C. The mixture was then allowed to stir about 20 minutes at about 49°–55° C.; the reaction mixture was then allowed to stand overnight.

The reaction mixture was filtered, rinsing the solids with 50/50 hexane/toluene. The filtrate was washed once with about 100 mls water, twice with about 100 mls of 2.5% HCl, twice with about 100 mls of 2.5% NaOH, once with about 50 mls water, and once with about 50 mls of brine. The organic layer was then dried over magnesium sulfate with added silica gel, and filtered, rinsing the solids with methylene chloride.

After stripping the solvent and hard topping, 61.94 grams of the product, an orange, cloudy oil, were obtained. Assay of the geometric isomers showed that the product was a mixture of the cis and trans isomers in the ratio of about 45:55, respectively.

EXAMPLE 4

Separation of Cis and Trans-1-isopropyl-3-(4-chloro)-phenoxy-4-(2-carbomethoxy)-phenyl-azet-2-one A mixture containing primarily trans isomer and one containing pure cis isomer was separated from the cis-trans mixture produced by Example 3 by dry column chromatography by the following procedure:

In a vessel, 3.4 grams of the product of Example 3, 7 grams of silica gel and 30 mls methylene chloride were placed and stirred. The resulting slurry was stripped to give a free-flowing solid.

The resulting solid was loaded on an 80 cm×5 cm column packed with silica gel (activity III). The material was eluted with about 1.25 liters methylene chloride:ethyl acetate (19:1).

(a) The further traveling band was isolated and the compound eluted with about 200 to 250 mls ethyl acetate. Stripping of the ethyl acetate gave 0.58 grams of a yellow oil which solidified at room temperature. NMR spectroscopy confirmed that the product was about 85% trans isomer and about 15% cis isomer.

Elemental analysis for $C_{20}H_{20}NClO_4$ showed: calculated %C 64.3, % H 5.4, and %N 3.8; found %C 62.0, %H 5.5, and %N 3.3.

(b) The shorter traveling band was isolated and eluted with about 400 to about 450 mls ethyl acetate. Stripping of the ethyl acetate gave 1.17 grams of a crystalline solid. NMR confirmed that the product was pure cis iomer.

EXAMPLE 5

Preparation of Cis-1-isopropyl-3-(4-chloro)-phenoxy-4-(2-carbomethoxy)-phenyl-azet-2-one In a 500-ml, 3-necked, round-bottom flask with drying tube, thermometer, stirrer and dropping funnel, about 20.9 grams of the product of Example 2, 10.1 grams triethylamine and 20 mls toluene were placed. To the resulting mixture, 19.4 grams α-(4-chlorophenoxy)acetyl chloride in 10 mls toluene were slowly added dropwise over 22 minutes. During the addition, the temperature of the reaction mixture was maintained at about 35°–40° C. The mixture was allowed to continue to stir for about 1 hour.

Then 100 mls ice water and about 20 mls methylene chloride were added to the reaction mixture. The phases were separated. The aqueous layer was washed with an additional aliquot of methylene chloride. The organic layers were combined and washed once with water and once with brine. The organic layer was dried over magnesium sulfate with added silica gel. Stripping of the solvent gave a light orange oil. NMR spectroscopy confirmed that it was cis isomer only with no visible trans isomer present. Hard topping of the oil gave 32.4 grams of a crystalline solid.

EXAMPLE A

The compounds of this invention, as well as a comparison compound*, were tested for axillary bud-growth inhibition and bean yield in pinto beans according to the following procedure:
*Disclosed in U.S. Ser. No. 225,886 as a plant growth regulator.

The soil of potted pinto bean plants was treated with 30 ml of a solution containing varying concentrations of test compound in water containing a small amount of acetone. The plants were incubated in a greenhouse maintained at 70°–80° F., and watered by irrigation during the course of the test.

Plants are evaluated for bean yield and number and weight of pods after 21 to 28 days, and compared to the standard TIBA. Results are given in Table I.

TABLE I

| Compound of Example # | Conc. $\mu/cm^2$ | # Pods/ Replicate | # Pods Std[1] | # Pods Check | Weight Pods | Weight Pods Std[1] | Weight Pods Check[2] |
|---|---|---|---|---|---|---|---|
| 3 | 35564 | 75 | 10.5 | 6.5 | 5.8 | 39.6 | 18.4 | 22.0 |

TABLE I-continued

| Compound of Example # | | Conc. $\mu/cm^2$ | # Pods/ Replicate | # Pods Std[1] | # Pods Check | Weight Pods | Weight Pods Std[1] | Weight Pods Check[2] |
|---|---|---|---|---|---|---|---|---|
| | | 30 | 10.0 | 9.5 | 5.8 | 38.6 | 32.7 | 22.0 |
| | | 12 | 8.3 | 7.8 | 5.8 | 34.2 | 31.0 | 22.0 |
| 5 | 38516 | 75 | 18.0 | 7.0 | 7.3 | 49.3 | 29.8 | 32.3 |
| | | 30 | 9.8 | 4.8 | 7.3 | 46.0 | 22.8 | 32.3 |
| | | 12 | 10.3 | 11.5 | 7.3 | 43.3 | 51.0 | 32.3 |
| Comparison | 29839 | 75 | 0.0 | 7.0 | 7.3 | 0.0 | 29.8 | 32.3 |
| | | 30 | 1.0 | 4.8 | 7.3 | 3.0 | 22.8 | 32.3 |
| | | 12 | 5.0 | 11.5 | 7.3 | 21.5 | 51.0 | 32.3 |

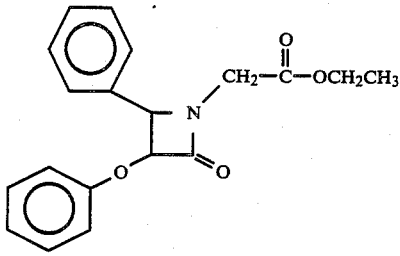

[1]Standard is TIBA at 12, 4.8 and 1.9 $\mu/cm^2$, respectively
[2]Treated with water-acetone solution without test compound The following compounds may be prepared in accordance with the procedures descried in Examples 1 to 5:
1-isopropyl-3-(4-chloro)-phenoxy-4-(2-carbethoxy)-phenyl-azet-2-one;
1-ethyl-3-(4-bromo)-phenoxy-4-(2-carbomethoxy)-phenyl-azet-2-one; and
1-isopropyl-3-phenoxy-4-(2-carbomethoxy)-phenyl-azet-2-one.

What is claimed is:

1. A plant growth regulating composition comprising a biologically inert carrier and a plant growth regulating effective amount of a compound of the formula:

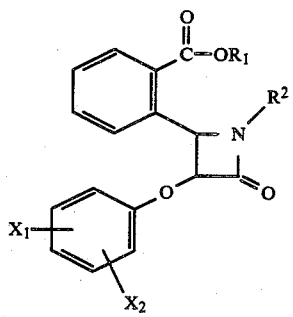

wherein $R_1$ is methyl or ethyl; $R_2$ is lower alkyl; and $X_1$ and $X_2$ are independently hydrogen or halogen.

2. A plant growth regulating composition according to claim 1 wherein one of $X_1$ and $X_2$ is halogen.

3. A plant growth regulating composition according to claim 2 wherein $X_1$ is 4-chloro and $X_2$ is hydrogen.

4. A plant growth regulating composition according to claim 3 wherein $R_2$ is isopropyl.

5. A plant growth regulating composition according to claim 4 wherein $R_1$ is methyl.

6. A plant growth regulating composition according to claim 1 wherein the compound is the trans isomer.

7. A plant growth regulating composition according to claim 2 wherein the compound is the trans isomer.

8. A plant growth regulating composition according to claim 7 wherein $X_1$ is 4-chloro and $X_2$ is hydrogen.

9. A plant regulating composition according to claim 8 wherein $R_2$ is isopropyl.

10. A plant growth regulating composition according to claim 9 wherein $R_1$ is methyl.

11. A method for regulating the growth of vegetation which comprises applying to said vegetation or its habitat a plant growth regulating effective amount of a compound of the formula:

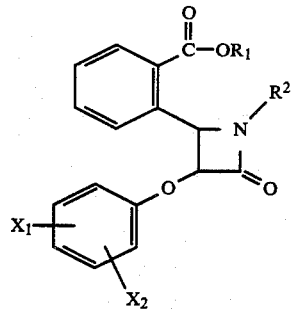

wherein $R_1$ is methyl or ethyl; $R_2$ is lower alkyl; and $X_1$ and $X_2$ are independently hydrogen or halogen.

12. The method of claim 11 wherein one of $X_1$ and $X_2$ is halogen.

13. The method of claim 12 wherein $X_1$ is 4-chloro and $X_2$ is hydrogen.

14. The method of claim 13 wherein $R_2$ is isopropyl.

15. The method of claim 14 wherein $R_1$ is methyl.

16. The method of claim 11 wherein the compound is the trans isomer.

17. The method of claim 12 wherein the compound is the trans isomer.

18. The method of claim 17 wherein $X_2$ is 4-chloro and $X_2$ is hydrogen.

19. The method of claim 18 wherein $R_2$ is isopropyl.

20. The method of claim 19 wherein $R_1$ is methyl.

21. A method of increasing yield in pinto bean plants or soybean plants which comprises applying to said plants or their habitat a yield increasing effective amount of a compound of the formula:

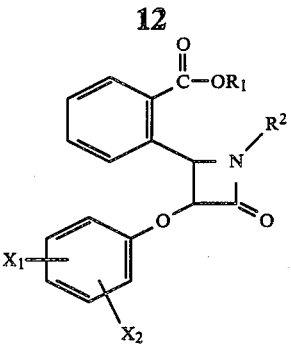

wherein $R_1$ is methyl or ethyl; $R_2$ is lower alkyl; and $X_1$ and $X_2$ are independently hydrogen or halogen.

22. The method of claim 21 wherein one of $X_1$ and $X_2$ is halogen.

23. The method of claim 22 wherein $X_1$ is 4-chloro, $X_2$ is hydrogen, $R_1$ is methyl and $R_2$ is isopropyl.

24. The method of claim 21 wherein the compound is the trans isomer, $X_1$ is 4-chloro, $X_2$ is hydrogen, $R_1$ is methyl and $R_2$ is isopropyl.

* * * * *